United States Patent
Pflaum et al.

(10) Patent No.: US 6,531,507 B1
(45) Date of Patent: Mar. 11, 2003

(54) STABILIZED PHARMACEUTICALLY EFFECTIVE COMPOSITION AND PHARMACEUTICAL FORMULATION COMPRISING THE SAME

(75) Inventors: Zlatko Pflaum, Domzale (SI); Janez Kerč, Ljubluana (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/591,322

(22) Filed: Jun. 9, 2000

(51) Int. Cl.⁷ ................... A61K 31/225; A61K 31/40
(52) U.S. Cl. ................ 514/547; 514/429; 514/423
(58) Field of Search .................. 514/423, 429

(56) References Cited

U.S. PATENT DOCUMENTS 5,798,375 A    8/1998   Tsujita et al. ............... 514/369

FOREIGN PATENT DOCUMENTS

| EP | 0 336 298 A1 | 10/1989 | .......... A61K/31/19 |
| EP | 0 336 298 B1 | 10/1989 | .......... A61K/31/19 |
| EP | 0 547 000 A1 | 6/1993 | .......... A61K/31/19 |
| GB | 2 055 100 A * | 2/1981 | |
| WO | WO 94/16693 | 8/1994 | .......... A61K/31/40 |
| WO | WO 97/03959 | 2/1997 | .......... C07D/207/34 |
| WO | WO 97/23200 | 7/1997 | .......... A61K/9/20 |
| WO | WO 00/17150 | 3/2000 | .......... C07C/69/01 |
| WO | WO 00/35425 | 6/2000 | .......... A61K/9/22 |

OTHER PUBLICATIONS

PCT/IB 00/00773 International Search Report.
PCT/IB 99/01749 International Search Report.

* cited by examiner

Primary Examiner—Frederick Krass
Assistant Examiner—Donna Jagoe
(74) Attorney, Agent, or Firm—Bromberg & Sunstein LLP

(57) ABSTRACT

Lovastatin, pravastatin, simvastatin, mevastatin, atorvastatin, and derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus, and some are obtained by treating the fermentation products using the methods of chemical synthesis or they are the products of total chemical synthesis.

The aforementioned active substances may be destabilized by the environmental factors, their degradation may also be accelerated by interactions with other pharmaceutical ingredients, such as fillers, binders, lubricants, glidants and disintegrating agents, therefore the pharmaceutical ingredients and the process for preparation of the pharmaceutical formulation should be meticulously chosen to avoid the aforementioned undesired interactions and reactions.

The present invention relates to a HMG-CoA reductase inhibitor which is stabilized by forming a homogeneous composition with a buffering substance or a basifying substance. This homogeneous composition is suitably used as the active substance in a pharmaceutical formulation for the treatment of hypercholesterolemia and hyperlipidemia.

26 Claims, 4 Drawing Sheets

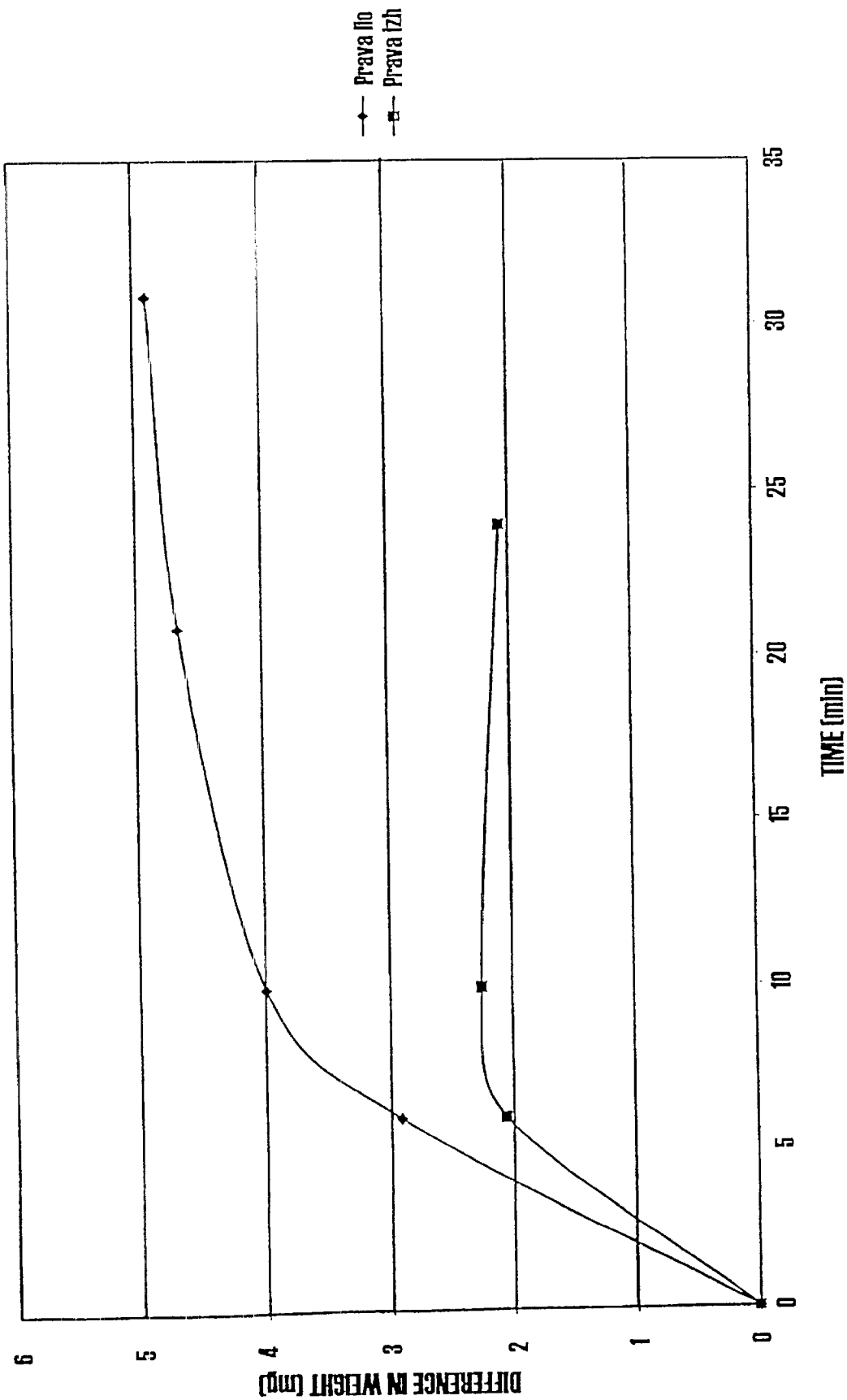

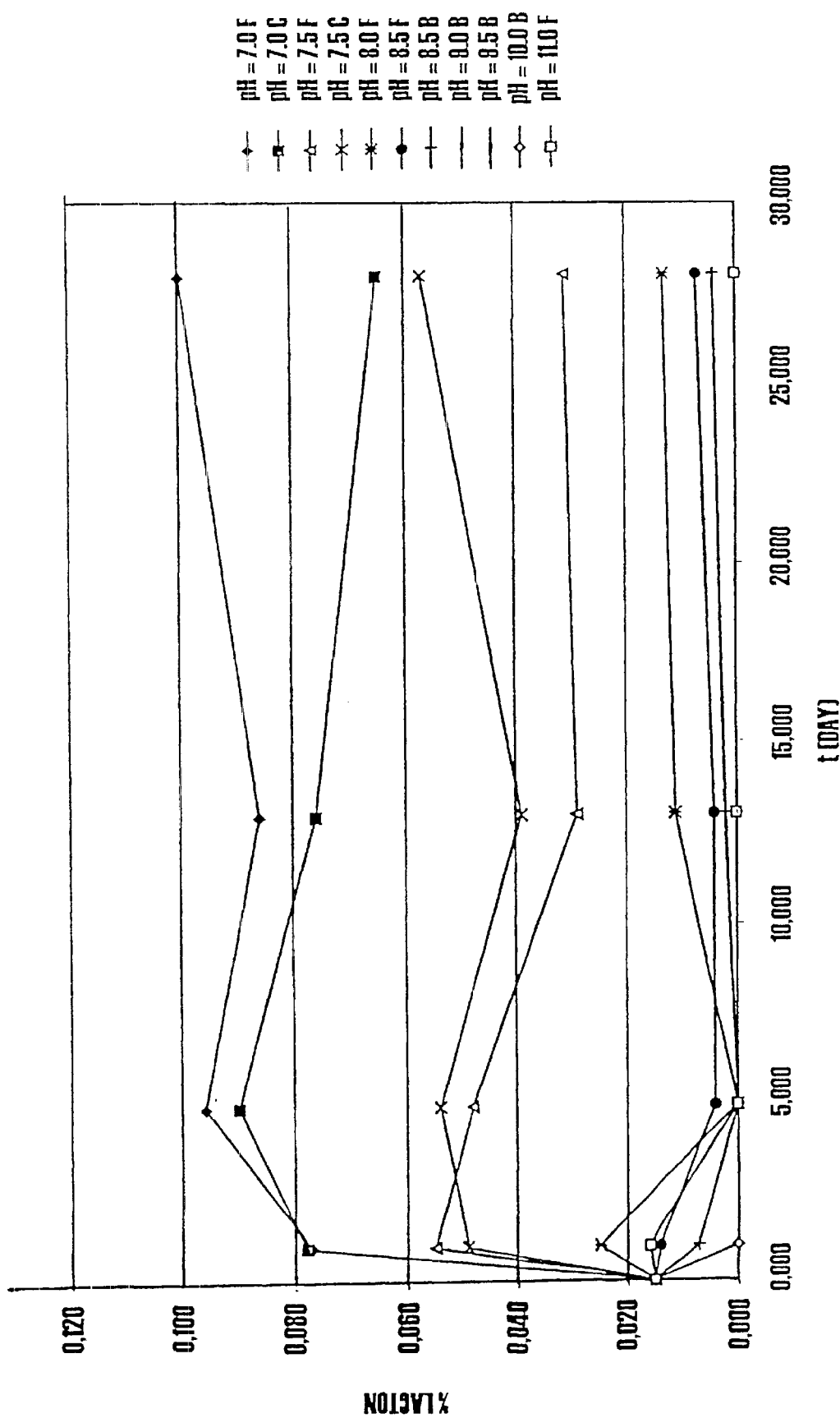

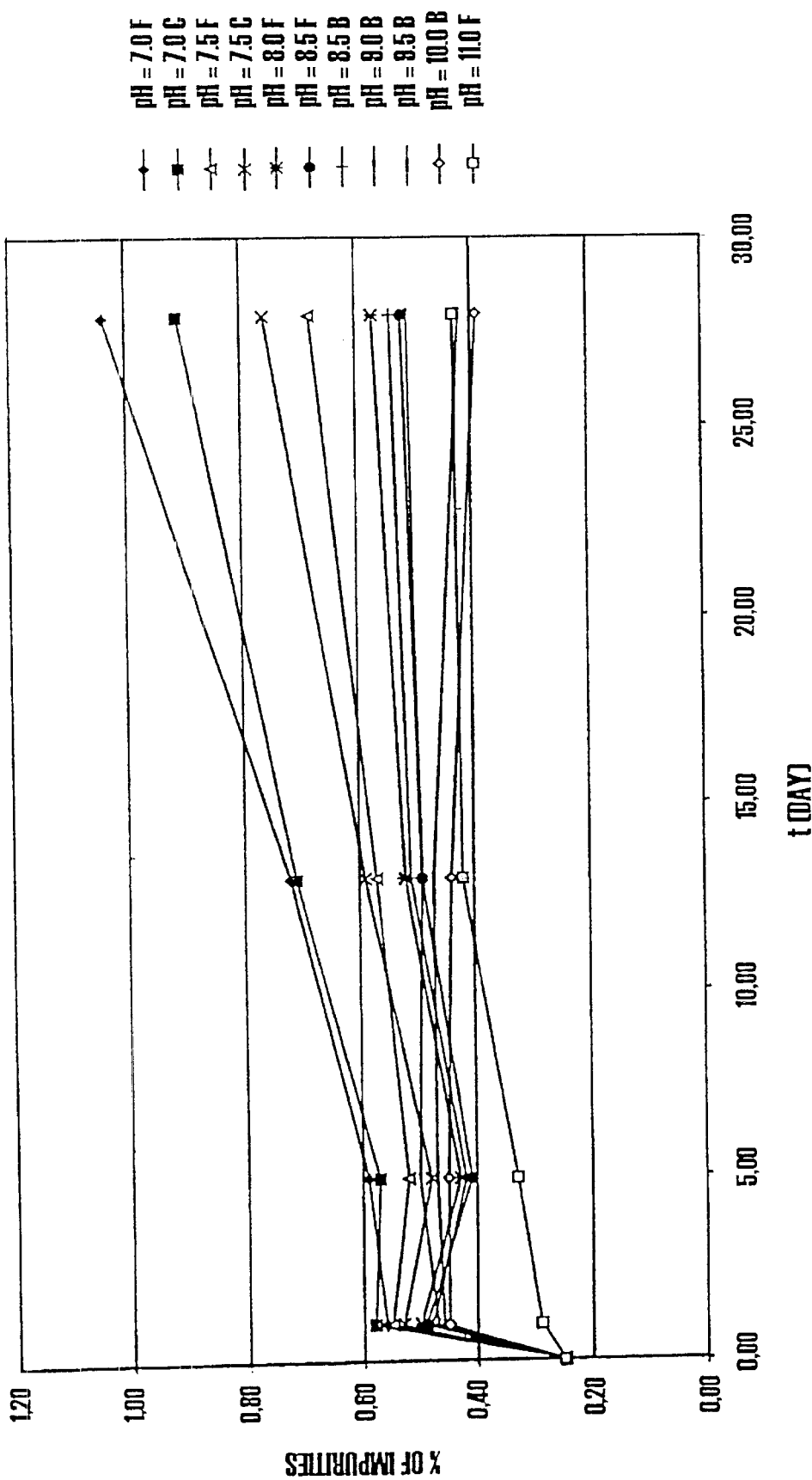
Figure 3 PRAVASTATIN, AT DIFFERENT pH, IMPURITIS

US 6,531,507 B1

STABILIZED PHARMACEUTICALLY EFFECTIVE COMPOSITION AND PHARMACEUTICAL FORMULATION COMPRISING THE SAME

FIELD OF THE INVENTION

The present invention relates to a newly stabilized HMG-CoA reductase inhibitor which is used in a pharmaceutical formulation being particularly suitable for the treatment of hypercholesterolemia and hyperlipidemia. More precisely, the present invention relates to a stabilized and very homogeneous composition mixture comprising a HMG-CoA reductase inhibitor, such as atorvastatin, pravastatin, fluvastatin and cerivastatin, or pharmaceutically active salts thereof, as well as solid pharmaceutical formulations containing the aforementioned homogeneous composition mixture as an active substance.

BACKGROUND OF THE INVENTION

Lovastatin, pravastatin, simvastatin, mevastatin, atorvastatin, fluvastatin and cerivastatin, derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycolatopsis, Mucor or Penicillium genus. Some are obtained by treating the fermentation products using the methods of chemical synthesis like simvastatin or they are the products of total chemical synthesis like fluvastatin, atorvastatin and cerivastatin.

The purity of the active substance is an important factor for manufacturing a safe and effective pharmaceutical formulation. Maximum possible purity of the product is of particular importance if the pharmaceutical product must be taken on a longer term basis in the treatment or prevention of high cholesterol levels in blood. Accumulation of impurities from drugs of a lower level of purity may cause a variety of side effects during treatment. Besides impurities, that cannot be completely eliminated in the process of preparation of the active substance, degradation products occurring by subjecting the final pharmaceutical formulation to various environmental factors such as temperature, moisture, low pH, carbon dioxide from the air and light, may also impose a significant problem. HMG-CoA reductase inhibitors occurring in the form of salts in the final pharmaceutical formulation, such as atorvastatin, pravastatin, fluvastatin and cerivastatin, are particularly sensitive to an acidic environment in which hydroxy acids are degraded into a lactone.

Apart from the fact that the aforementioned active substance may be destabilized by the environmental factors, their degradation may also be accelerated by interactions with other pharmaceutical ingredients, such as fillers, binders, lubricants, glidants and disintegrating agents. Therefore, the pharmaceutical ingredients and the process for preparation of the pharmaceutical formulation should be meticulously chosen to avoid the aforementioned undesired interactions and reactions.

The stability of the active substance in an acidic environment is one of the major problems in the case of statins in the form of salts. One of possible solutions of the aforementioned problem is described in EP 0 336 298, disclosing a stable pharmaceutical formulation for pravastatin. The essence of the formulation is to maintain an alkaline environment so that the aqueous dispersion of the pharmaceutical formulation reaches a pH above 9, preferably about 10. In addition to the active substance pravastatin, the composition of the invention includes a basifying agent, such as magnesium oxide, which imparts a pH to an aqueous dispersion of the aforementioned formulation above 9. In view of the stability of the active substance such a formulation is effective. However, the local alkaline environment occurring at the site of dissolution of the pharmaceutical formulation may have a negative impact on the gastric mucosa with its normally acidic environment, especially since a relatively high amount of basifying agent is necessary to ensure acceptable stability. This negative impact may be particularly evident for patients with a damaged gastric mucous membrane where the mucosa per se is not able to create a sufficient acidic environment inside the stomach for normal digestive functioning. It is particularly important in chronic therapies as in the case of prophylaxis or treatment with HMG-CoA reductase inhibitors.

Another approach; for providing a stable pharmaceutical formulation is described in the present Applicant's earlier PCT application No. PCT/IB99/01749.

SUMMARY OF THE INVENTION

It is an object of the present invention to provide a pharmaceutical formulation containing as an active substance a HMG-CoA reductase inhibitor which exerts an excellent stability while avoiding the afore mentioned disadvantages. It is a particular object to provide a stabilized active substance as such, i.e. before being formulated into the pharmaceutical formulation, where the HMG-CoA reductase inhibitor is precautionary protected from being degraded.

It is a further object to provide a process for the preparation of a stabilized HMG-CoA reductase inhibitor which exerts an excellent stability while avoiding the aforementioned disadvantages.

These and further objects are accomplished by the present invention.

According to the present invention, there is provided a a composition comprising a homogeneous mixture of a HMG-CoA reductase inhibitor with a buffering substance or a basifying substance, which composition has been obtained by co-crystallization and/or co-precipitation of said HMG-CoA reductase inhibitor and said buffering substance or basifying substance.

By means of co-crystallization and/or co-precipitation, the obtained dried HMG-CoA reductase inhibitor compound itself is mixed with the buffering substance or the basifying substance in a very homogeneous and finely distributed form. It is believed that the buffering substance or the basifying substance is finely distributed around the HMG-CoA reductase inhibitor crystals, thus forming a kind of protective "microenvironment". The protective effect is much more efficient as in the case of merely mixing or granulating starting powders, even in a wet process, as performed in EP-A-0 336 298. Moreover, since already the HMG-CoA reductase inhibitor as such (in bulk) is efficiently protected against deleterious environmental factors due to the excellent homogeneous distribution with the buffering substance or the basifying substance, the HMG-CoA reductase inhibitor can be handled more conveniently and stably stored as such, if desired, before being added to the pharmaceutical formulation. In particular, the homogeneous composition according to the present invention is highly resistant to the negative effect of carbon dioxide and moisture from the air, and a much better protection against low pH conditions is achieved when the composition containing the HMG-CoA reductase inhibitor is incorporated as the active substance into the final pharmaceutical formulation.

Accordingly, the present invention also makes available a newly stabilized pharmaceutical formulation comprising the aforementioned specific composition as the active substance.

According to the-present invention, there is further provided a process for preparing a stabilized HMG-CoA reductase inhibitor which comprises the step of crystallization and/or precipitation of the HMG-CoA reductase inhibitor with the buffering substance or the basifying substance.

BRIEF DESCRIPTION OF THE DRAWINGS

FIG. 1B shows the corresponding difference in the starting weight and the weight in time.

FIG. 2 is a diagram which shows the occurrence of pravastatin in lactone form when pravastatin was dissolved in different buffers with the pH in a range between 7 and 11 (F=phosphate, C=citrate, B=borate).

FIG. 3 is a diagram which shows the formation of different degradation products (impurities) when pravastatin was dissolved in different buffers with the pH in a range between 7 and 11 (F=phosphate, C=citrate, B=borate).

DETAILED DESCRIPTION OF THE PREFERRED EMBODIMENTS

Figure 1A:
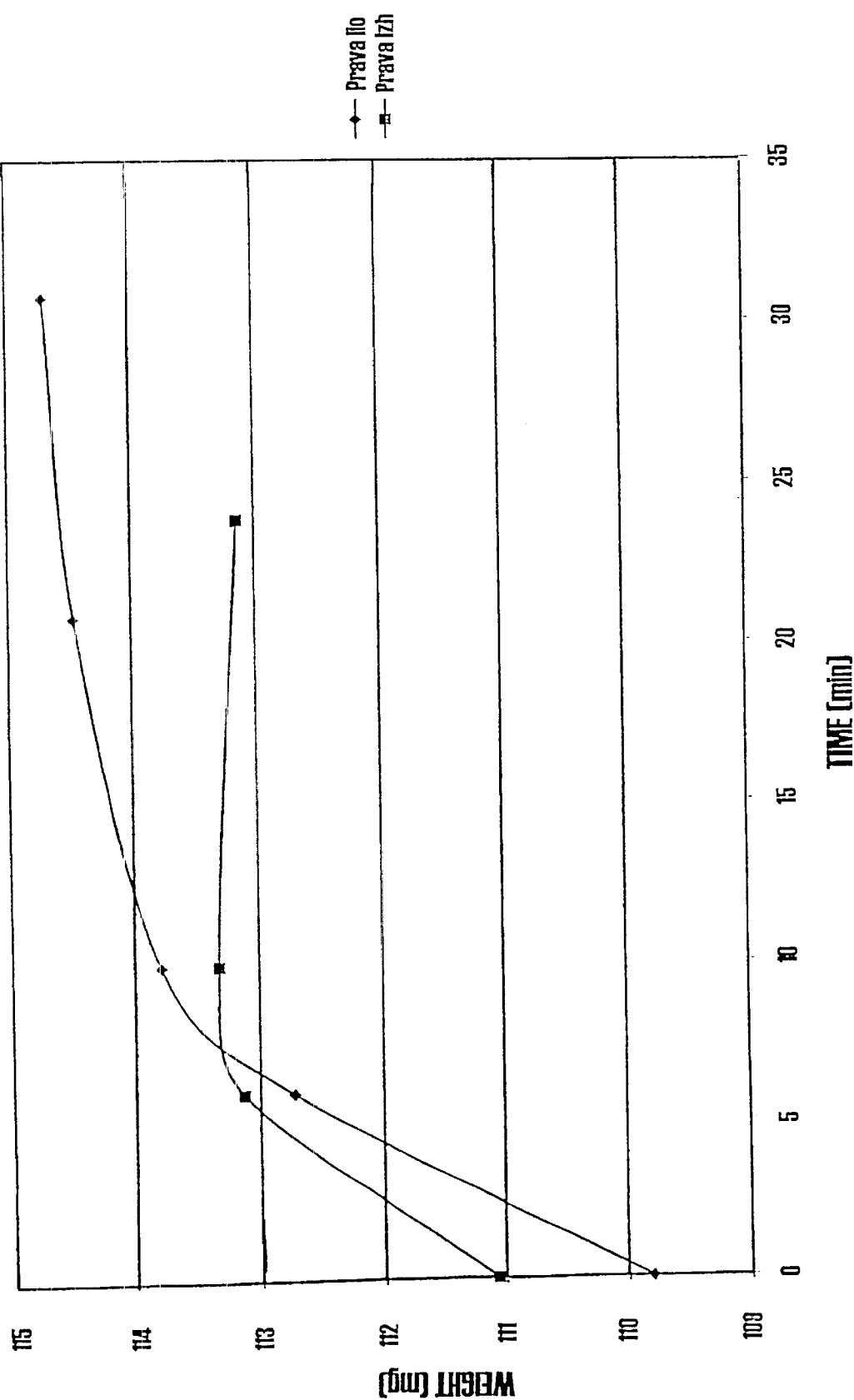
FIGS. 1A is a diagram which shows the growth of weight of a sample of pravastatin in crystal form and a sample of lyophilised pravastatin when exposed to air moisture.

In the inventor's investigations, it was found that there are three major reasons for instability problems in case of a pharmaceutical formulation containing an active substance and in case of a bulk active substance.

First, the active substance as such is very hygroscopic and it is impossible to remove all water from it. This is illustrated by the following experiment: 111.07 mg of pravastatin in crystal form (prava izh) and 109.8 mg of lyophilized pravastatin (prava lio) were exposed to air moisture. Their weights were measured in different time intervals. The growth of weight of both samples and the difference in the starting weight and the weight in time are illustrated in FIGS. 1A and 1B.

Another observation was that carbon dioxide from the air may irreversibly and reversibly bind to the active substance and can cause a drop of pH. This is illustrated by the following experiment: 5 g of pravastatin sodium were dissolved in 30 ml of methanol, the pH was adjusted to 10 with 3% aqueous solution of NaOH. 400 ml of ethylacetate were added and the crystals of pravastatin sodium were formed. Crystals werelfiltered and dried and then put into three different atmospheres: normal air, nitrogen atmosphere and carbon dioxide atmosphere. In normal air and in the nitrogen atmosphere the pH remained the same during a period of 24 hours (normal air: 9.2, nitrogen: 9.5), but in the carbon dioxide atmosphere the pH dropped in the first two minutes from 9.2 to 6.9. After 12 minutes the pH was 6.6 and after 1 hour the pH was 6.5. After that, the pH remained constant.

The third observation is that a sufficient stabilization of the active substance is already obtained at a pH of at least 7.0, but a beneficially high stability is effected at a pH of at least 8.0. We have noticed that at a pH below 8 the formation of lactone has occurred and also the amount of other impurities has increased. The presence of humidity in the air and a carbon dioxide-rich atmosphere makes the negative effect of a low pH even stronger. This is illustrated by the following experiment: Pravastatin was dissolved in different buffers with the pH in a range between 7 and 11 (F=phosphate, C=citrate, B=borate). The occurrence of pravastatin in lactone form and the formation of different degradation products (impurities) was measured after 1, 5, 13 and 28 days. The results are shown in FIGS. 2 and 3.

In the present invention, we have surprisingly found that a sufficient stability of the active substance, which is a HMG-CoA reductase inhibitor preferably in the form of salt, can be also obtained by using a pharmaceutical formulation which does not create a marked alkaline environment in an aqueous dispersion. In order to achieve this efficiently, it is significant that the HMG-CoA reductase inhibitor is present in a homogeneous mixture by co-crystallization and/or co-precipitation with the buffering substance or the basifying substance in the composition according to the present invention, before the mixed composition is incorporated into the pharmaceutical formulation as the active substance. The composition of the present invention, which is the pharmaceutically active substance, may essentially consist only of said homogeneous, co-crystallized or co-precipitated HMG-CoA reductase inhibitor and buffering substance or basifying substance, but may contain further components and additives as desired.

Another surprising finding was that a sufficient stability of a HMG-CoA reductase inhibitor in the form of a salt in bulk can be obtained even when amount of the buffering substance or the basifying substance crystallized or precipitated with the HMG-CoA reductase inhibitor is low. In the conventional stabilization concept described in EP-A-0 336 298, the basifying substance is added to the pharmaceutical formulation in an amount from 1 to 75 wt.-%, and in the Examples the weight ratio of the basifying substance relative to pravastatin is from 33 to 500%.

According to the present invention, a protective effect can be achieved at lower ratios of the buffering substance or the basifying substance, such as below 30 wt.-%, while this ratio is preferably 10 wt.-% or less, more preferably 5 wt.-% or less and in particular 1 wt.-% or less, relative to the;amount of co-crystallized or co-precipitated HMG-CoA reductase inhibitor. The lower limit mainly depends on the environmental conditions and the kind and amounts of other components to be used for the pharmaceutical formulation, but an amount of at least 0.05 or 0.1 wt.-% of the buffering substance or the basifying substance, relative to the amount of HMG-CoA reductase inhibitor, is generally sufficient to provide a desired protective effect. Such an addition of small amounts of buffering substances or basifying substances avoids the negative effect of water already present in the bulk substance and of moisture from the air, avoids the negative effect of low pH caused by other ingredients which will be co-admixed to the pharmaceutical formulation, and avoids the possible lowering of the pH caused by carbon-dioxide. Accordingly, the active substance and the pharmaceutical formulation according to the present invention were designed to avoid the negative effect of the water present in the bulk substance and in the pharmaceutical formulation, to avoid the negative effect of low pH which can be caused by other ingredients of the pharmaceutical formulation and to avoid possible lowering of the pH caused by carbon dioxide.

Furthermore, we have recognized that the protecting effect, especially the resistance against the negative effect of carbon dioxide, is better when the buffering substance or the basifying substance is co-crystallized and/or co-precipitated rather than merely admixed by mixing, milling or granulating, which is assumed to be attributable to a more homogeneous, fine distribution in the composition according to the present invention. Accordingly, a corresponding stabilizing effect can be achieved with lower amounts of buffering substance or basifying substance.

Thus, it is possible to mix HMG-CoA reductase inhibitor with other ingredients of the pharmaceutical formulation without fear that a degradation can be caused by the contact of HMG-CoA reductase inhibitor with acidic ingredients, because a microenvironment of HMG-CoA reductase inhibitor is effectively made slightly basic or markedly basic due to the addition of small amounts of a buffering substance or basifying substance. This addition of a buffering substance or basifying substance is also important for an easier handling of the HMG-CoA reductase inhibitor bulk composition without special requirements for a carbon dioxide free atmosphere.

Further, we have found that for the stability and digestibility of a pharmaceutical formulation both the pH generated by the formulation in an aqueous medium (usually being a dispersion) and the pH of the active substance (i.e. the HMG-CoA reductase inhibitor-containing composition alone) preferably should be adjusted.

The most acceptable stability of the active substance in the formulations is obtained with the above composition, as the active substance, which is capable of providing a pH in the range from 7 to 12 and preferably from 8 to 11. The pH value is the one which is obtained when the pH of an aqueous medium containing said composition would be measured. In the stable pharmaceutical formulation according to the present invention, the basic pH of the active substance has a minimal influence on the pH of the formulation. By creating locally an environment around the active substance which affords the best stability for the active substance, the potential of negative impact of other ingredients of the composition of the pharmaceutical formulation is reduced, and possible reactions among the active substance and the rest of the ingredients of the composition of the pharmaceutical formulation are also less favored. Accordingly, the specific composition or active substance is maintained in a stable form when an active substance which is capable of providing a pH in an aqueous medium in the range from 7 to 12 and preferably in the range from 8 to 11 is added to the pharmaceutical formulation.

The HMG-CoA reductase inhibitor used for obtaining the specific composition or active substance of the present invention generally is in the form of a salt and may be selected from the group consisting of pravastatin, atorvastatin, fluvastatin, cerivastatin. Since the stabilizing effect becomes particularly pronounced in these cases, the HMG-CoA reductase inhibitor is preferably a calcium salt of atorvastatin (atorvastatin Ca) and most preferred a sodium salt of pravastatin (pravastatin Na). Nonetheless, stability can be improved in accordance with the present invention also in the case of other HMG-CoA reductase inhibitors.

A process suitable for preparing the aforementioned specific composition including the stabilized HMG-CoA reductase inhibitor will now be further described. The characteristic step is the crystallization and/or precipitation of both the HMG-CoA reductase inhibitor and the buffering substance or basifying substance from the same medium. This step may be performed as the final step in the course of conventionally isolating and purifying the HMG-CoA reductase inhibitor, but it may also be performed by using an already isolated HMG-CoA reductase inhibitor which suitably has a (HPLC) purity of at least 98%, preferably of at least 99.5%. First, a solution or dispersion of the HMG-CoA reductase inhibitor and the buffering substance or basifying substance is provided. A common solvent or medium may be used for providing this solution or dispersion, for example low alkyl alcohols such as methanol, ethanol, propanol and isopropyl alcohol, low alkyl ketones such as acetone and methyl ethyl ketone, low alkyl glycol ethers such as methyl glycol, ethyl glycol, propyl glycol and ethyl diglycol, and dipolar aprotic solvents such as N,N-dimethyl-formamide (DMF), N,N-dimethylacetamide (DMA) and dimethyl sulfoxide (DMSO), including mixtures of these solvents. Acetone and low alkyl alcohols such as methanol are preferred. Then, an orlganic solvent, in which the compounds are less or hardly soluble or insoluble, is added in order to allow the HMG-CoA reductase inhibitor and the buffering substance or basifying substance to crystallize and/or precipitate together. Examples for the organic solvent include: higher alkyl alcohols such as butanol, isobutanol amyl alcohol, hexanol, 2-ethylhexanol, benzyl alcohol and cyclohexanol, higher alkyl ketones such as methylbutyl ketone, methyl isobutyl ketone and cyclohexanone, esters such as methyl acetate, ethyl acetate, n-propyl (and isopropyl) acetate, n-butyl (and iso-butyl or sec-butyl) acetate and amyl acetate, ethers such as diethyl ether and diisopropyl ether, chlorinated hydrocarbons such as methylene chloride and chloroform, acetonitrile and the like, including mixtures of these solvents. Ethyl acetate is particularly preferred as the organic solvent.

The pH of the composition (active substance) is adjusted, preferably within the above specified range, by means of the co-crystallized or co-precipitated buffering substance or basifying substance in the aforementioned amounts.

The buffering substance or agent is suitable selected from the group consisting of salts of inorganic acids, salts of organic bases or salts of organic acids. Examples of salts of inorganic acids include sodium or potassium citrate, sodium or potassium phosphate or hydrogen phosphate, dibasic sodium phosphate, sodium, potassium, magnesium or calcium carbonate or hydrogen carbonate, sulphate, or mixtures of such buffering agents, or the like; carbonate buffer or phosphate buffer, such as sodium carbonate of sodium phosphate, being preferred. Examples for salts of organic bases include aminoguanidine carbonate or hydrogen carbonate, guanidine carbonate or hydrogen carbonate, succinimide carbonate or hydrogen carbonate, 1-adamantil amine carbonate or hydrogen carbonate, N,N'-bis(2-hydroxyethyl) ethylendiamine carbonate or hydrogen carbonate, tris (hydroxymethyl) aminometan carbonate or hydrogen carbonate, D(-)-N-Methylglucamine carbonate or hydrogen carbonate, or the like. Examples for salts of organic acids include potassium or sodium salts of acetic acid, citric acid, lactic acid, ascorbic acid, maleic acid, phenylacetic acid, benzoic acid, lauryl sulphuric acid, or the like.

The basifying substance or agent is suitable selected from the group consisting of metal oxides, inorganic bases, organic bases and organic acids with basic character. Examples of metal oxides include magnesium oxide and aluminum oxide. Examples of inorganic bases include alkali metal hydroxide such as sodium hydroxide, potassium hydroxide, alkali earth metal hydroxide such as calcium hydroxide or magnesium hydroxide. Examples of organic bases include succinimide, 1-adamantyl amine, N,N'-bis(2-hydroxyethyl) ethylendiamine, tris (hydroxymethyl) aminomethane, D(-)-N-methylglucamine, or the like. Examples of organic acids with basic character include 3-(N-morpholino)propanesulfonic acid, 4-[[cyclohexyl amino]]-1-butansulfonic acid, 4-[[cyclohexyl amino]]-1-etansulfonic acid and the alkaline metal or alkaline earth metal salts of these acids, arginine, ornithine, lysine, or the like.

The buffering or basifying substance may also be generated in situ, for example by adding an alkali metal or alkali earth metal hydroxide to the solution and then blowing carbon dioxide into the solution until a desired pH is adjusted.

The composition or active substance of the present invention as described above is then added to the final pharmaceutical formulation by means of an appropriate formulation process. Besides the composition (pharmaceutically active substance) of the present invention, the pharmaceutical formulation according to the present invention mayIfurther comprise at least one constituent selected from the group consisting of a filler, a binder, a disintegrating agent, a glidant, a buffering agent; optionally further comprising at least one constituent selected among coloring agents, lakes, aromas, adsorbents, film formers and plasticizers.

By means of adding further buffering or basifying substances to the formulation, it is possible to effectively improve and maintain the resistance of the final formulation against carbon dioxide by neutralizing the acidifying effect thereof. Any one of the above described buffering or basifying substances may be additionally used for the pharmaceutical formulation. In order to avoid a negative impact on the patient's gastric mucosa during the administration of the pharmaceutical formulation, it is preferable to use additional buffering substance, and to adjust the pH of the formulation, i.e. the provided pH when the pharmaceutical formulation is brought in solution or dispersion, to a range below 9, preferably below 8.5, whereas the lower limit of the pH generated by the pharmaceutical formulation suitably is 6, preferably 7. The amount of additional buffering or basifying substance may be 20 wt.-% or less, more preferably 10 wt.-% per weight or less based on the total weight of the tablet.

The pharmaceutical formulation of this invention may include, in addition to the HMG-CoA reductase inhibitor which is sensitive to a low pH environment, one or more fillers, such as microcrystalline cellulose, lactose, sugars, starches, modified starch, mannitol, sorbitol and other polyols, dextrin, dextran and maltodextrin, calcium carbonate, calcium phosphate and/or hydrogen phosphate, sulphate, one or more-binders such as lactose, starches, modified starch, dextrin, dextran and maltodextrin, microcrystalline cellulose, sugars, polyethylene glycols, hydroxypropyl cellulose, hydroxypropyl methylcellulose, ethylcellulose, hydroxyethyl cellulose, methylcellulose, carboxymethyl cellulose, gelatin, acacia gum, tragacanth, polyvinylpyrrolidone, magnesium aluminium silicate, one or more disintegrating agents such as croscarmellose sodium, cross-linked polyvinylpyrrolidone, cross-linked carboxymethyl starch, starches and microcrystalline cellulose, magnesium aluminium silicate, polyacrylin potassium, one or more different glidants such as magnesium stearate, calcium stearate, zinc stearate, calcium behenate, sodium stearyl fumarate, talc, magnesium trisilicate, stearic acid, palmitic acid, carnauba wax, silicon dioxide, one or more buffering agents such as sodium or potassium citrate, sodium phosphate, dibasic sodium phosphate, calcium carbonate, hydrogen phosphate, phosphate, sulphate, sodium or magnesium carbonate, sodium ascorbinate, benzoate, sodium or potassium hydrogen carbonate, lauryl sulphate, or mixtures of such buffering agents.

If required any, the formulation may also include surfactants and other conventional components for solid, pharmaceutical formulations such as coloring agents, lakes, aromas and adsorbents. As surfactants the following may be used: ionic surfactants, such as sodium lauryl sulphate or non-ionic surfactants such as different poloxamers (polyoxyethylene and polyoxypropylene copolymers), natural or synthesized lecithins, esters of sorbitan and fatty acids (such as Span®, manufactured by Atlas Chemie), esters of polyoxyethylenesorbitan and fatty acids (such as Tween®, manufactured by Atlas-Chemie), polyoxyethylated hydrogenated castor oil (such as Cremophor®, manufactured by BASF), polyoxyethylene stearates (such as Brij®, manufactured by Atlas Chemie), dimethylpolysiloxane or any combination of the above mentioned surfactants.

If the solid pharmaceutical formulation is in the form of coated tablets, the coating may be prepared from at least one film-former such as hydroxypropyl methylcellulose, hydroxypropyl cellulose, at least from one plasticizer such as polyethylene glycols, dibutyl sebacate, triethyl citrate, and other pharmaceutical auxiliary substances conventional for film coatings, such as pigments, fillers and others.

The solid pharmaceutical formulations according to the present invention may be prepared as described below:

The mixture of the active substance, filler, binder, buffering agent, disintegrating agent and if required a surfactant and other conventional ingredients for solid pharmaceutical formulations is homogenized employing suitable mixers. Glidants and/or lubricants are added and the mixture is re-homogenized. The resulting mixture is compressed into tablets or filled into capsules. If needed, tablets can be film-coated.

The mixture of the active substance, filler, binder, buffering agent, disintegrating agent and if required a surfactant and other conventional ingredients for solid pharmaceutical formulations is homogenized employing suitable mixers, granulated with a suitable solvent such as water, ethanol, methanol, isopropyl alcohol, n-butyl alcohol, acetone, diethyl ether, ethyl acetate, isopropyl acetate, methyl acetate, dichloromethane and methanol, and mixtures of these solvents such as ethanol and acetone, methanol and acetone, dichloromethane and methanol, and the mixtures thereof. The resulting granulation is dried in suitable dryers such as standard plate dryers, fluid bed dryers, vacuum and microwave dryers. To the dried granulation, glidants and/or lubricants and if required other conventional ingredients for solid pharmaceutical formulations are added. The resulting mixture is rehomogenized and compressed into tablets or filled into capsules. Optionally, tablets are film-coated.

The present invention is illustrated but by no means limited by the following examples.

EXAMPLES

The following instrumentation was used in the examples: LDC HPLC System: column (30×4.6) mm Lichrospher, detector 236 nm, sample ≈500 mg/L injector 5 µL, mobile phase A: 15% ACN, mobile phase B: 90% ACN, gradient 0': 100% A, 3.5' 100% B, flow 2.8 ml/min; pH meter: Iskra MA 5741

(I) Stabilizing of HMG-CoA Reductase Inhibitor by Addition of Salts of Inorganic Acids

Example 1

Stabilizing of Pravastatin Sodium by Addition of Sodium Carbonate

Pravastatin Sodium (I-17226103B, 5 g) with chromatographic purity 99.5% and pH 7.4 (1%)/7.7 (5%) was dissolved in methanol (30 ml), sodium carbonate (10 mg, dissolved in 0.15 ml of water) was added and finally, ethylacetate (400 ml containing 2% of water) was added. After 1 hour the resulted crystals were filtered off, washed with fresh ethylacetate (50 ml) and dried at 40° C. for 6 hours in vacuo. The chromatographic purity of resulted crystals (4.3 g) was 99.6% and pH was 9.5(1%)/9.8 (5%). The results of the stability measurements are shown in Table 1.

Example 2

Stabilizing of Pravastatin Sodium by Addition of Sodium Hydrogen Carbonate

Pravastatin Sodium (I-17226103B, 5 g) with chromatographic purity 99.5% and pH 7.4 (1%)/7.7 (5%) was dissolved in methanol (30 ml), sodium hydrogen carbonate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.4 g) was 99.6% and pH was 9.2 (1%)/9.6 (5%).

The results of the stability measurements are shown in Table 1.

Example 3

Stabilizing by Addition of di-Sodium Hydrogen Phosphate

Pravastatin Sodium (I-17226103B, 5 g) with chromatographic purity 99.5% and pH 7.4 (1%)/7.7 (5%) was dissolved in methanol (30 ml), di-sodium hydrogen phosphate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 8.0 (1%)/8.4 (5%). The results of the stability measurements are shown in Table 1.

Example 4

Stabilizing with Sodium Hydroxide and Carbon Dioxide

Pravastatin Sodium (I-17226103B, 5 g) with chromatographic purity 99.5% and pH 7.4 (1%)/7.7 (5%) was dissolved in methanol (30 ml), sodium hydroxide was added to reach pH=9.5, carbon dioxide was blown into the solution to reach pH of 8.3 (equilibrium) and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 7.7 (1%)/8.3 (5%).

The results of the stability measurements are shown in Table 1.

(II) Stabilizing of Pravastatin Sodium by Addition of Salts of Organic Base

Example 5

Stabilizing by Addition of Aminoguanidine Hydrogen Carbonate

Pravastatin Sodium (I-17226103B, 5 g) with chromatographic purity 99.5% and pH 7.4 (1%)/7.7 (5%) was dissolved in methanol (30 ml), aminoguanidine hydrogen carbonate (10 mg, dissolved in 1 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.2 g) was 99.6% and pH was 8.1 (1%)/8.8 (5%).

The results of the stability measurements are shown in Table 1.

(III) Stabilizing of Pravastatin Sodium by addition of salts of organic acids

Example 6

Stabilizing by Addition of Sodium Acetate

Pravastatin Sodium (I-17226103B, 5 g) with chromatographic purity 99.5% and pH 7.4 (1%)/7.7 (5%) was dissolved in methanol (30 ml), sodium acetate (10 mg, dissolved in 0.15 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 7.9 (1%)/8.3 (5%).

The results of the stability measurements are shown in Table (IV) Stabilizing of Pravastatin Sodium by Addition of the Inorganic Base Example 7

Stabilizing by Addition of Magnesium Oxide (or Hydroxide)

Pravastatin Sodium (I-17226103B, 5 g) with chromatographic purity 99.5% and pH 7.4 (1%)/7.7 (5%) was dissolved in methanol (30 ml), magnesium oxide (10 mg) was added and finally, ethylacetate (400 ml, containing 2% of water) was added. After 1 hour the resulted crystals were filtered off, washed with fresh ethylacetate (50 ml) and dried at 40° C. for 6 hours in vacuo.

The chromatographic purity of resulted crystals (4.3 g) was 99.6% and pH was 8.7 (1%)/9.3 (5%).

The results of the stability measurements are shown in Table 1.

(V) Stabilizing of Pravastatin Sodium by Addition of the Organic Base

Example 8

Stabilizing by Addition of L-Arginine

Pravastatin Sodium (I-17226103B, 5 g) with chromatographic purity 99.5% and pH 7.4 (1%)/7.7 (5%) was dissolved in methanol (30 ml), L-arginine (10 mg, dissolved in 0.15 ml of water) was added and finally, ethylacetate (400 ml, containing 2% of water) was added. After 1 hour the resulted crystals were filtered off, washed with fresh.ethylacetate (50 ml) and dried at 40° C. for 6 hours in vacuo.

The chromatographic purity of resulted crystals (4.3 g) was 99.6% and pH was 8.9 (1%)/9.3 (5%).

The results of the stability measurements are shown in Table 1.

(VI) Results of Examples 1 to 8

TABLE 1

| Experiment | | After preparing | | After 1 week on air atm. | |
|---|---|---|---|---|---|
| Sample | buffer/basif. agent | pH (1%) | pH (5%) | pH (1%) | pH (5%) |
| I-17226103B | Raw crystals | 7.4 | 7.7 | 7.2 | 7.6 |
| Example 1 | Na₂CO₃ | 9.5 | 9.8 | 9.5 | 9.8 |
| Example 2 | NaHCO₃ | 9.2 | 9.6 | 9.3 | 9.7 |
| Example 3 | Na₂HPO₄ | 8.0 | 8.4 | 8.0 | 8.4 |
| Example 4 | NaOH/CO₂ | 7.7 | 8.3 | 7.7 | 8.4 |
| Example 5 | aminoguan. HCO₃ | 8.1 | 8.8 | 8.2 | 8.9 |
| Example 6 | CH₃COONa | 7.9 | 8.3 | 8.0 | 8.4 |
| Example 7 | MgO | 8.7 | 9.3 | 8.8 | 9.5 |
| Example 8 | L-Arginine | 8.9 | 9.3 | 8.9 | 9.3 |

(VII) Stabilizing of Pravastatin Sodium by Addition of Salts of Organic Acids with Basic Character Example 9

Stabilizing of Pravastatin Sodium by Addition of 3-(N-Morpholino) propanesulfonic Acid (MOPS) Sodium salt Pravastatin Sodium (I-17226103B, 5 g) with chromatographic purity 99.5% and pH 7.4 (1%)/7.7 (5%) was dissolved in methanol (30 ml), 3-(N-Morpholino) propanesulfonic acid Sodium salt (50 mg, dissolved in 0.3 ml of water) was added and finally, ethylacetate (400 ml containing 2% of water) was added. After 1 hour the resulted crystals were filtered off, washed with fresh ethylacetate (50 ml) and dried at 40° C. for 6 hours in vacuum.

The chromatographic purity of resulted crystals (4.3 g) was 99.5% and pH was 8.1 (1%)/8.5 (5%).

(VIII) Stabilizing of Pravastatin Sodium by Addition of the Organic Base

Example 10

Stabilizing by Addition of Tris(hydroxymethyl) aminomethane

Pravastatin Sodium (I-17226103B, 5 g) with chromatographic purity 99.5% and pH 7.4 (1%)/7.7 (5%) was dissolved in methanol (30 ml), tris(hydroxymethyl) aminomethane (50 mg, dissolved in 0.4 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuum.

The chromatographic purity of resulted crystals (4.3 g) was 99.6% and pH was 8.0 (1%)/8.3 (5%).

Example 11

Stabilizing by Addition of N,N'-bis(2-hydroxyethyl) ethylenediamine

Pravastatin Sodium (I-17226103B, 5 g) with chromatographic purity 99.5% and pH 7.4 (1%)/7.7 (5%) was dissolved in methanol (30 ml), N,N'-bis(2-hydroxyethyl) ethylenediamine (50 mg, dissolved in 0.4 ml of water) was added and finally, ethylacetate (400 ml, containing 2% of water) was added. After 1 hour the resulted crystals were filtered off, washed with fresh ethylacetate (50 ml) and dried at 40° C. for 6 hours in vacuum.

The chromatographic purity of resulted crystals (4.3 g) was 99.6% and pH was 8.3 (1%)/8.9 (5%).

(IX) Results of Examples 9 to 11

TABLE 2

| Experiment | | After preparing pH | | After 1 week on air atm. pH | |
|---|---|---|---|---|---|
| Sample | buffer/basifying agent | (1%) | (5%) | (1%) | (5%) |
| | Raw crystals | 7.4 | 7.7 | 7.2 | 7.6 |
| Ex. 9 | MOPS Sodium salt | 8.1 | 8.5 | 8.1 | 8.6 |
| Ex. 10 | Tris(hydroxymethyl) aminomethane | 8.0 | 8.3 | 8.0 | 8.3 |
| Ex. 11 | N,N'-bis (2-hydroxyethyl) ethylenediamine | 8.3 | 8.9 | 8.3 | 8.8 |

(X) Evaluation

The main cause for the unstability of HMG-CoA reductase inhibitor in bulk, such as pravastatin sodium, is carbon dioxide from the air and the consecutive lowering of the pH of the active substance. The result of lowering of the pH is conversion pravastatin sodium to the lacton form.

Using various buffers or basifying agents in co-precipitation and or co-crystallization with the HMG-CoA reductase inhibitor, it is possible to make a very homogeneous composition as the pharmaceutically active substance where the HMG-CoA reductase inhibitor is effectively protected from being destabilized, see the results shown in Tables 1 and 2. At the same time, the pH of bulk active substance may be set to an appropriate value as desired. For example, pravastatin sodium is stable especially at a pH of between 8 and 10. In the above examples 0.2 wt.-% of buffering or basifying agent relative to pravastatin sodium was used, but lower or higher amount also work effectively.

The compositions according to the present invention obtained as described above can be incorporated in typical amounts into the pharmaceutical formulation, for example as described in the earlier PCT application No. PCT/IB99/01749 incorporated herein by reference, where the active substance is replaced by the compositions according to the present invention.

What is claimed is:

1. A composition comprising a homogeneous mixture of a HMG-CoA reductase inhibitor with a buffering substance or a basifying substance in a finely distributed form, obtained by co-crystallization and/or co-precipitation of said HMG-CoA reductase inhibitor and said buffering substance or basifying substance.

2. The composition according to claim 1, wherein said buffering substance or basifying substance is contained in the homogeneous mixture in an amount of 10 wt.-% or less, relative to the amount of HMG-CoA reductase inhibitor.

3. The composition according to claim 1, wherein said buffering substance or basifying substance is contained in the homogeneous mixture in an amount of 1 wt.-% or less, relative to the amount of HMG-CoA reductase inhibitor.

4. The composition according to claim 1 which essentially consists only of said homogeneous mixtures.

5. The composition according to claim 1, wherein said buffering substance used for co-crystallization and/or co-precipitation is selected from the group consisting of salts of inorganic acids, salts of organic bases and/salts of organic acids.

6. The composition according to claim 1, wherein said basifying substance used for co-crystallization and/or co-precipitation is selected from the group consisting of metal oxides, inorganic bases, organic bases and organic acids with basic character.

7. The composition according to claim 1 which is capable of providing a pH in the range from 7 to 12.

8. The composition according to claim 1 which is capable of providing a pH in the range from 8 to 11.

9. The composition according to claim 1, wherein said HMG-CoA reductase inhibitor used for co-crystallization and/or co-precipitation is in the form of a salt.

10. The composition according to claim 1, wherein said HMG-CoA reductase inhibitor is selected from the group consisting of pravastatin, atorvastatin, fluvastatin, cerivastatin and pharmaceutically acceptable salts thereof.

11. The composition according to claim 1, wherein said HMG-CoA reductase inhibitor used for co-crystallization and/or co-precipitation had a purity of at least 98%.

12. A pharmaceutical formulation comprising as an active substance a composition as defined in claim 1.

13. A pharmaceutical formulation comprising as an active substance a pravastatin sodium-containing composition as defined in claim 12.

14. The pharmaceutical formulation according to claim 12, which is capable of providing a pH in the range from 6 to 9.

15. The pharmaceutical formulation according to claim 12, which is capable of providing a pH in the range from 7 to 8.5.

16. The pharmaceutical formulation according to claim 12, which further comprises an additional amount of a buffering substance.

17. The pharmaceutical formulation according to claim 12, which further comprises at least one constituent selected from the group consisting of a filler, a binder, a disintegrating agent, a glidant, a buffering agent; optionally further comprising at least one constituent selected among coloring agents, lakes, aromas, adsorbents, film formers and plasticizers.

18. A composition comprising a homogeneous mixture of a pravastatin sodium with a buffering substance or a basifying substance in a finely distributed form, obtained by co-crystallization and/or co-precipitation of said pravastatin sodium and said buffering substance or basifying substance.

19. A process for preparing a stabilized HMG-CoA reductase inhibitor in a homogeneous mixture with a buffering substance or a basifying substance in a finely distributed form, comprising the steps of crystallization and/or precipitation of said HMG-CoA reductase inhibitor together with a buffering substance or a basifying substance.

20. The process according to claim 19, wherein the step of crystallization and/or precipitation comprises providing a solution containing said HMG-CoA reductase inhibitor and said buffering substance or basifying substance, and then adding an organic solvent to the solution in order to allow said HMG-CoA reductase inhibitor and said buffering substance or basifying substance to crystallize and/or precipitate.

21. The process according to claim 20, wherein the organic solvent is ethyl acetate.

22. The process according to 19, wherein said buffering substance is selected from the group consisting of salts of inorganic acids, salts of organic bases and salts of organic acids.

23. The process according to claim 19, wherein said basifying substance is selected from the group consisting of metal oxides, inorganic bases, organic bases and organic acids with basic character.

24. The process according to claim 19, herein said HMG-CoA reductase inhibitor used for co-crystallization and/or co-precipitation is in the form of a salt.

25. The process according to claim 19, wherein said HMG-CoA reductase inhibitor is selected from the group consisting of pravastatin, atorvastatin, fluvastatin, cerivastatin and pharmaceutically acceptable salts thereof.

26. The process according to claim 25, wherein said HMG-CoA reductase inhibitor is a sodium salt of pravastatin (pravastatin Na) or a calcium salt of atorvastatin (atorvastatin Ca).

* * * * *